(12) United States Patent
Neumann

(10) Patent No.: US 11,688,507 B2
(45) Date of Patent: Jun. 27, 2023

(54) SYSTEMS AND METHODS FOR GENERATING A METABOLIC DYSFUNCTION NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,224

(22) Filed: Dec. 29, 2020

(65) Prior Publication Data

US 2022/0208342 A1 Jun. 30, 2022

(51) Int. Cl.
  *G16H 20/60* (2018.01)
  *G16H 50/30* (2018.01)
  (Continued)

(52) U.S. Cl.
  CPC ........... *G16H 20/60* (2018.01); *G06N 20/00* (2019.01); *G16H 10/40* (2018.01); *G16H 40/63* (2018.01); *G16H 50/20* (2018.01); *G16H 50/30* (2018.01)

(58) Field of Classification Search
  CPC ........ G16H 20/60; G16H 10/40; G16H 50/30; G16H 50/20; G16H 40/63; G16H 10/60;
  (Continued)

(56) References Cited

U.S. PATENT DOCUMENTS 8,762,167 B2 * 6/2014 Blander ................. G06Q 10/10
                                                          705/2
8,920,175 B2 * 12/2014 Black ................. G09B 19/0092
                                                          434/127
(Continued)

FOREIGN PATENT DOCUMENTS

CN       104872677 A    9/2015
IN    201641005016 A    8/2017

OTHER PUBLICATIONS

Gao et al. "Natural genetic variation in C. elegans identified genomic loci controlling metabolite levels", Genome Research, https://genome.cshlp.org/content/28/9/1296.short (Year: 2018).*
(Continued)

*Primary Examiner* — Fonya M Long
*Assistant Examiner* — Alaaeldin M Elshaer
(74) *Attorney, Agent, or Firm* — Caldwell Intellectual Property Law

(57) ABSTRACT

A system and method for generating a metabolic dysfunction nourishment program comprises a computing device configured to obtain a metabolic component as a function of a user metabolic system, identify a metabolic panel as a function of the metabolic component, wherein identifying further comprises receiving a status grading, ascertaining a metabolic functional goal, and identifying the metabolic panel as a function of the status grading, metabolic functional goal, and metabolic component using a metabolic machine-learning model, determine an edible as a function of the metabolic panel, wherein determining further comprises receiving a nourishment composition from an edible directory, producing a nourishment demand as a function of the metabolic panel, and determining the edible as a function of the nourishment composition and nourishment demand using an edible machine-learning model, and generate a
(Continued)

nourishment program as a function of the edible and a metabolic outcome using a nourishment machine-learning model.

18 Claims, 7 Drawing Sheets

(51) Int. Cl.
    *G16H 50/20*         (2018.01)
    *G06N 20/00*        (2019.01)
    *G16H 10/40*        (2018.01)
    *G16H 40/63*        (2018.01)

(58) Field of Classification Search
    CPC .......... G16H 20/10; G06N 20/00; G06N 5/04;
                 G06N 3/08; G06N 20/10; G06Q 50/22;
                G06F 16/9032; G06F 16/9035; G06F
                               16/2255; A61B 5/00
    USPC ........................................................ 705/2, 3
    See application file for complete search history.

(56) References Cited

U.S. PATENT DOCUMENTS

| | | | |
|---|---|---|---|
| 9,999,653 B2 | | 6/2018 | Cincotta |
| 11,018,900 B2 * | | 5/2021 | Iyengar ............... H04L 12/6418 |
| 2007/0281038 A1 | | 12/2007 | Trouille |
| 2008/0275728 A1 | | 11/2008 | Ordovas |
| 2009/0192365 A1 | | 7/2009 | Gisel |
| 2010/0113892 A1 | | 5/2010 | Kaput |
| 2010/0228160 A1 * | | 9/2010 | Schweizer ............ G16H 20/60 |
| | | | 600/595 |
| 2014/0310019 A1 | | 10/2014 | Blander |
| 2016/0049092 A1 * | | 2/2016 | Barnett ..................... G09B 5/02 |
| | | | 434/127 |
| 2017/0224001 A1 | | 8/2017 | Tian |
| 2017/0316150 A1 * | | 11/2017 | Deciu .................. C12Q 1/6869 |
| 2018/0251819 A1 | | 9/2018 | Pichaud |
| 2018/0256660 A1 | | 9/2018 | Housey |
| 2018/0374386 A1 * | | 12/2018 | Benefield ........... A63B 24/0059 |
| 2019/0223489 A1 | | 7/2019 | Ames |
| 2019/0228856 A1 * | | 7/2019 | Leifer .................... G16H 20/60 |
| 2019/0255084 A1 | | 8/2019 | Schentag |
| 2020/0029614 A1 | | 1/2020 | Longo |
| 2021/0045694 A1 * | | 2/2021 | Hadley ................. A61B 5/1118 |
| 2021/0050089 A1 * | | 2/2021 | Mohammed ......... A61B 5/4833 |
| 2021/0146072 A1 * | | 5/2021 | Krüger ................ A61M 16/022 |

OTHER PUBLICATIONS

Reference Notes: Clinical Nutrition ESPEN, vol. 38, Aug. 2020, pp. 61-64 Title: A systematic review of precision nutrition and Mediterranean Diet: A personalized nutrition approaches for prevention and management of obesity related disorders Date: Aug. 2020 By: Cangul Tuncay.

* cited by examiner

SYSTEMS AND METHODS FOR GENERATING A METABOLIC DYSFUNCTION NOURISHMENT PROGRAM

FIELD OF THE INVENTION

The present invention generally relates to the field of artificial intelligence. In particular, the present invention is directed to a system and method for generating a metabolic dysfunction nourishment program.

BACKGROUND

Current edible suggestion systems do not account for the metabolic system of an individual. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect a system for generating a metabolic dysfunction nourishment program comprises a computing device configured to obtain a metabolic component as a function of a user metabolic system, identify a metabolic panel as a function of the metabolic component, wherein identifying further comprises receiving a status grading as a function of a metabolic guideline, ascertaining a metabolic functional goal, and identifying the metabolic panel as a function of the status grading, metabolic functional goal, and metabolic component using a metabolic machine-learning model, determine an edible as a function of the metabolic panel, wherein determining further comprises receiving a nourishment composition from an edible directory, producing a nourishment demand as a function of the metabolic panel, and determining the edible as a function of the nourishment composition and nourishment demand using an edible machine-learning model, and generate a nourishment program as a function of the edible and a metabolic outcome using a nourishment machine-learning model.

In another aspect a method for generating a metabolic dysfunction nourishment program comprises obtaining, by a computing device, a metabolic component as a function of a user metabolic system, identifying, by the computing device, a metabolic panel as a function of the metabolic component, wherein identifying further comprises receiving a status grading as a function of a metabolic guideline, ascertaining a metabolic functional goal, and identifying the metabolic panel as a function of the status grading, metabolic functional goal, and metabolic component using a metabolic machine-learning model, determining, by the computing device, an edible as a function of the metabolic panel, wherein determining further comprises receiving a nourishment composition from an edible directory, producing a nourishment demand as a function of the metabolic panel, and determining the edible as a function of the nourishment composition and nourishment demand using an edible machine-learning model, and generating, by the computing device, a nourishment program as a function of the edible and a metabolic outcome using a nourishment machine-learning model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a metabolic dysfunction nourishment program. In an embodiment, the disclosure may obtain a metabolic component as a function of a user metabolic system. Aspects of the present disclosure can be used to identify a metabolic panel as a function of the metabolic component. This is so, at least in part, because the metabolic panel is identified as a function of a machine-learning model. Aspects of the present disclosure can also be used to determine an edible as a function of the metabolic panel. Aspects of the present disclosure allow for generating a nourishment program as a function of the edible and a metabolic outcome using a nourishment machine-learning model.

Figure 1:
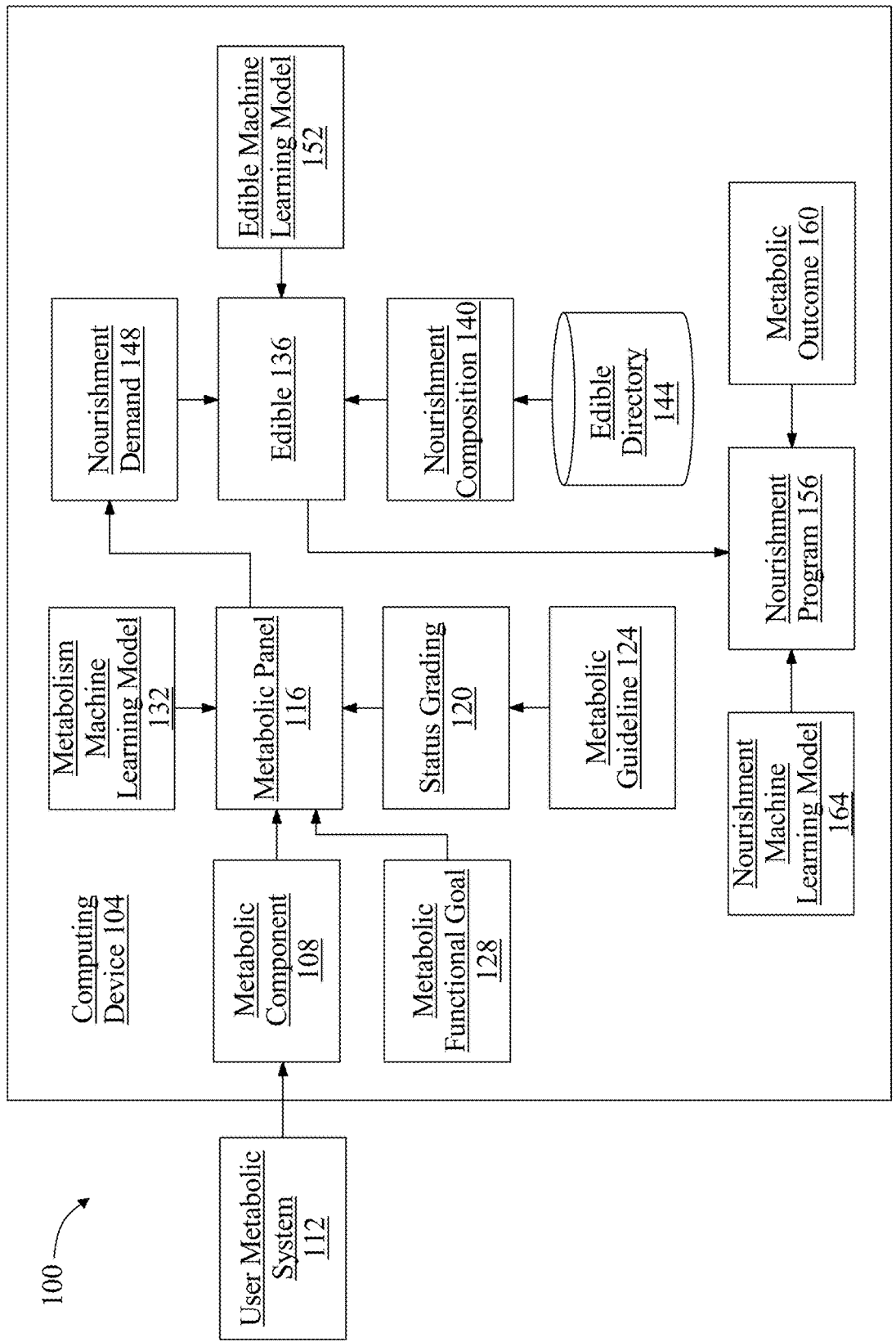
FIG. 1 is a block diagram illustrating an exemplary embodiment of a system for generating a metabolic dysfunction nourishment program.

Referring now to FIG. 1, an exemplary embodiment of a system 100 for generating a metabolic dysfunction nourishment program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains a metabolic component 108. As used in this disclosure a "metabolic component" is an element of data that denotes an individual's metabolic system health status. Metabolic component 108 may include a biological sample. As used in this disclosure a "biological sample" is one or more biological specimens collected from an individual. Biological sample may include, without limitation, exhalate, blood, sputum, urine, saliva, feces, semen, and other bodily fluids, as well as tissue. Metabolic component 108 may include a biological sampling device. Metabolic component 108 may include one or more biomarkers, wherein biomarkers are molecules and/or chemicals that at least identify the health status of a user's metabolic system. As a non-limiting example, biomarkers may include, dihydropyrimidine dehydrogenase, mannose-binding lectin protein, UGT1A1, chromosome 2q37, Bilirubin, hepatocyte nuclear factor 1-alpha, hepatocyte nuclear factor 4-alpha, hepatocyte nuclear factor 1-beta, glycolytic enzyme glucokinase dihydroxyacetone phosphate acyltransferase, C26:0/C22:0 psitanic acid beta-oxidation, phytanic acid alpha-oxidation, and the like thereof. As a further non-limiting example metabolic component 108 may include datum from one or more devices that collect, store, and/or calculate one or more lights, voltages, currents, sounds, chemicals, pressures, and the like thereof that are associated with the user's metabolic system. Metabolic component 108 may include one or more comprehensive metabolic panels (CMP), wherein a CMP is a test that measures 14 substances in a user's blood. For example, and without limitation, CMP may determine concentrations of glucose, calcium, sodium, potassium, carbon dioxide, chloride, albumin, total protein, alkaline phosphatase, bilirubin, blood urea nitrogen, creatinine, and the like thereof. Metabolic component 108 is received as a function of a metabolic system 112. As used in this disclosure a "metabolic system" is an organ and/or tissue system that relates to life-sustaining chemical reactions in a user's body. As a non-limiting example metabolic system 112 may include organs and/or tissues relating to the conversion of food to energy to run cellular process, conversion of food and/or fuel to building blocks for proteins, lipids, nucleic acids, carbohydrates, and the like thereof, and/or elimination of metabolic wastes. Metabolic system 112 may include organs and/or tissues associated with one or more catabolic processes. As used in this disclosure a "catabolic process" are metabolic processes associated with breaking down large molecules for the purpose of providing energy to the user. As a non-limiting example catabolic processes may include digestion, oxidative phosphorylation, chemolithotrophy, and the like thereof. Metabolic system 112 may include organs and/or tissues associated with one or more anabolic processes. As used in this disclosure an "anabolic process" is a metabolic process associated with constructing complex molecules from simple molecules. As a non-limiting example, anabolic processes may include the synthesis of proteins, polysaccharides, lipids, nucleic acids, and the like thereof.

Still referring to FIG. 1, computing device 104 may obtain a metabolic component 108 by receiving an input from a user. As used in this disclosure "input" is an element of datum that is obtained by the user. As a non-limiting example input may include a user entering a feeling of thirst, fatigue, lethargy, blurred vision, hot flashes, loss of memory, and the like thereof. Input may include one or more inputs from an informed advisor as a function of a medical assessment, wherein a "medical assessment" is an evaluation and/or estimation of the health status of a metabolic system. As used in this disclosure "informed advisor" is an individual that is skilled in a particular area relating to the study of metabolism. As a non-limiting example an informed advisor may include a medical professional who may assist and/or participate in the medical treatment of an individual's metabolic system including, but not limited to, endocrinologists, metabolic physicians, functional medicine practitioners, chemical pathologists, cardiovascular physicians, family physicians, family physicians, and the like thereof. As a non-limiting example input may include an informed advisor that enters a metabolic assessment comprising a resting metabolic rate test, $VO_2$ max test, lactate threshold test, anaerobic threshold test, and the like thereof.

Still referring to FIG. 1, computing device 104 identifies a metabolic panel 116 as a function of metabolic component 108. As used in this disclosure a "metabolic panel" is a profile of the metabolic system health status, wherein a health status is a relative level of wellness and illness of the metabolic system. As a non-limiting example metabolic panel 116 may include a profile comprising concentrations of blood sugar, triglycerides, high density lipoprotein, cholesterol, blood pressure, waist circumference, and/or respiratory rate. As a further non-limiting example, metabolic panel 116 may include a profile comprising concentrations of amino acids, proteins, lipids, nucleotides, coenzymes, catabolic rates, anabolic rates, minerals, and/or cofactors. Computing device 104 identifies metabolic panel 116 by receiving a status grading 120. As used in this disclosure a "status grading" is a grade and/or rank associated with a health status of a user metabolic system. As a non-limiting example, status grading 120 may include a low health status, wherein a low health status may indicate a user has a high risk for developing metabolic complications, wherein a "metabolic complication" is one or more process that occur that are abnormal to a user's metabolic system. Status grading 120 may be received as a function of a metabolic guideline 124. As used in this disclosure a "metabolic guideline" is a medical guideline for the measurement of metabolic health status, as described in detail below, in reference to FIG. 4. As a non-limiting example metabolic guideline 124 may be identified by one or more organizations that relate to, represent, and/or study metabolic function in humans, such as American Society for Metabolic and Bariatric Surgery, Society for Inherited Metabolic disorders, American Medical Association, and the like thereof. As a further non-limiting example, metabolic guideline 124 may output status grading 120 as a function of one or more medical research journals, such as The Journal of Metabolic Research, Journal of Obesity and Metabolic Research, Internal Medicine, The Lancet, New England Journal of Medicine, Science, Journal of the American Medical Association, and the like thereof.

Still referring to FIG. 1, computing device 104 identifies metabolic panel 116 by ascertaining a metabolic functional goal 128. As used in this disclosure a "metabolic functional goal" is a user desire, wish, want, and/or urge to alter and/or address a user concern. For example, and without limitation, metabolic functional goal 128 may include enhancing anabolic reactions of the muscle. As a further non-limiting example, metabolic functional goal 128 may include reducing anabolic reactions of lipids associated with oleic acid, palmitic acid, and/or linoleic acid. As a further non-limiting example, metabolic functional goal 128 may include increasing caloric expenditure over a particular time period, wherein a time period may include seconds, minutes, hours, days, weeks, months, years, and the like thereof. Computing device 104 identifies metabolic panel 116 as a function of status grading 120, metabolic functional goal 128, and metabolic component 108 using a metabolic machine-learning model 132. As used in this disclosure "metabolic machine-learning model" is a machine-learning model to produce a metabolic panel output given status gradings, metabolic functional goals, and metabolic components as inputs; this is in contrast to a non-machine learning software program where the commands to be executed are determined in advance by a user and written in a programming language. Metabolic machine-learning model 132 may include one or more metabolic machine-learning processes such as supervised, unsupervised, or reinforcement machine-learning processes that computing device 104 and/or a remote device may or may not use in the determination of metabolic panel 116. As used in this disclosure "remote device" is an external device to computing device 104. A metabolic machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train metabolic machine-learning process as a function of a metabolic training set. As used in this disclosure "metabolic training set" is a training set that correlates a status grading, metabolic functional goal, and/or metabolic component to a metabolic panel. For example, and without limitation, a metabolic functional goal of enhanced catabolic reactions of fat, a status grading of low health due to obesity, and a metabolic component of elevated cholesterol may relate to a metabolic panel of obesity. The metabolic training set may be received as a function of user-entered valuations of status gradings, metabolic functional goals, metabolic components, and/or metabolic panels. Computing device 104 may receive metabolic training by receiving correlations of status gradings, metabolic functional goals, and or metabolic components that were previously received and/or determined during a previous iteration of determining metabolic panels. The metabolic training set may be received by one or more remote devices that at least correlate a status grading, metabolic functional goal, and/or metabolic component to a metabolic panel, wherein a remote device is an external device to computing device 104, as described above. The metabolic training set may be received by one or more user-entered correlations of a status grading, metabolic functional goal, and/or metabolic component to a metabolic panel. Additionally or alternatively, a user may include an informed advisor, wherein an informed advisor may include, without limitation, endocrinologists, metabolic physicians, functional medicine practitioners, chemical pathologists, cardiovascular physicians, family physicians, family physicians, and the like thereof.

Still referring to FIG. 1, computing device 104 may receive metabolic machine-learning model from a remote device that utilizes one or more metabolic machine learning processes, wherein a remote device is described above in detail. For example, and without limitation, a remote device may include a computing device, external device, processor, and the like thereof. Remote device may perform the metabolic machine-learning process using the metabolic training set to generate metabolic panel 116 and transmit the output to computing device 104. Remote device may transmit a signal, bit, datum, or parameter to computing device 104 that at least relates to metabolic panel 116. Additionally or alternatively, the remote device may provide an updated machine-learning model. For example, and without limitation, an updated machine-learning model may be comprised of a firmware update, a software update, a metabolic machine-learning process correction, and the like thereof. As a non-limiting example a software update may incorporate a new metabolic component that relates to a modified metabolic functional goal. Additionally or alternatively, the updated machine learning model may be transmitted to the remote device, wherein the remote device may replace the metabolic machine-learning model with the updated machine-learning model and determine the metabolic panel as a function of the metabolic component using the updated machine-learning model. The updated machine-learning model may be transmitted by the remote device and received by computing device 104 as a software update, firmware update, or corrected metabolic machine-learning model. For example, and without limitation metabolic machine-learning model may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device 104 may identify metabolic panel 116 by identifying a metabolic dysfunction. As used in this disclosure a "metabolic dysfunction" is an ailment and/or collection of ailments that impact an individual's metabolic system. As a non-limiting example, metabolic dysfunction may include familial hypercholesterolemia, Gaucher disease, Hunter syndrome, Krabbe disease, maple syrup urine disease, metachromatic leukodystrophy, mitochondrial encephalopathy, Niemann-Pick, sickle cell anemia, hemochromatosis, Gilbert syndrome, acatalasemia, monogenic diabetes, carnosinemia, Fish-eye disease, fucosidosis, Kanzaki disease, mevalonic aciduria, Perrault syndrome, Wilson disease, Zellweger syndrome, and the like thereof. Metabolic dysfunction may be determined as a function of one or more dysfunction machine-learning models. As used in this disclosure, a "dysfunction machine-learning model" is a machine-learning model to produce a metabolic dysfunction output given metabolic component 108 as inputs; this is in contrast to a non-machine learning software program where the commands to be executed are determined in advance by a user and written in a programming language. Dysfunction machine-learning model may include one or more dysfunction machine-learning processes such as supervised, unsupervised, or reinforcement machine-learning processes that computing device 104 and/or a remote device may or may not use in the determination of metabolic dysfunction. A dysfunction machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train dysfunction machine-learning process as a function of a dysfunction training set. As used in this disclosure, a "dysfunction training set" is a training set that correlates at least a metabolic enumeration and a metabolic system effect to a metabolic dysfunction. As used in this disclosure, a "metabolic enumeration" is a measurable value associated with the metabolic component. As used in this disclosure, a "metabolic system effect" is an impact and/or effect on the metabolic system of an individual. As a non-limiting example a metabolic enumeration of 17 may be relate to a metabolic system effect of frequent vomiting and/or metabolic acidosis, wherein a metabolic dysfunction of valinemia may be determined. The dysfunction training set may be received as a function of user-entered valuations of metabolic enumerations, metabolic system effects, and/or metabolic dysfunctions. Computing device 104 may receive dysfunction training by receiving correlations of metabolic enumerations and/or metabolic system effects that were previously received and/or determined during a previous iteration of determining metabolic dysfunctions. The dysfunction training set may be received by one or more remote devices that at least correlate a metabolic enumeration and/or metabolic system effect to an metabolic dysfunction, wherein a remote device is an external device to computing device 104, as described above. The dysfunction training set may be received in the form of one or more user-entered correlations of a metabolic enumeration and metabolic system effect to a metabolic dysfunction. Additionally or alternatively, a user may include an informed advisor, wherein an informed advisor may include, without limitation, endocrinologists, metabolic physicians, functional medicine practitioners, chemical pathologists, cardiovascular physicians, family physicians, family physicians, and the like thereof.

Still referring to FIG. 1, computing device 104 may receive dysfunction machine-learning model from the remote device that utilizes one or more dysfunction machine learning processes, wherein a remote device is described above in detail. For example, and without limitation, a remote device may include a computing device, external device, processor, and the like thereof. The remote device may perform the dysfunction machine-learning process using the dysfunction training set to generate metabolic dysfunction and transmit the output to computing device 104. The remote device may transmit a signal, bit, datum, or parameter to computing device 104 that at least relates to metabolic dysfunctions. Additionally or alternatively, the remote device may provide an updated machine-learning model. For example, and without limitation, an updated machine-learning model may be comprised of a firmware update, a software update, a dysfunction machine-learning process correction, and the like thereof. As a non-limiting example a software update may incorporate a new metabolic enumeration that relates to a modified metabolic system effect. Additionally or alternatively, the updated machine learning model may be transmitted to the remote device, wherein the remote device may replace the dysfunction machine-learning model with the updated machine-learning model and determine the metabolic dysfunction as a function of the metabolic enumeration using the updated machine-learning model. The updated machine-learning model may be transmitted by the remote device and received by computing device 104 as a software update, firmware update, or corrected dysfunction machine-learning model. For example, and without limitation dysfunction machine-learning model may utilize a Naïve bayes machine-learning process, wherein the updated machine-learning model may incorporate decision tree machine-learning process.

Still referring to FIG. 1, computing device 104 determines an edible 136 as a function of metabolic panel 116. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. Computing device 104 identifies edible 136 as a function of obtaining a nourishment composition 140. As used in this disclosure a "nourishment composition" is a list and/or compilation of all of the nutrients contained in an edible. As a non-limiting example nourishment composition 140 may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition 140 may be obtained as a function of an edible directory 144, wherein an "edible directory" is a database of edibles that may be identified as a function of one or more metabolic components, as described in detail below, in reference to FIG. 3.

Still referring to FIG. 1, computing device 104 determines a nourishment demand 148 as a function of metabolic panel 116. As used in this disclosure a "nourishment demand" is requirement and/or necessary amount of nutrients required for a user to consume. As a non-limiting example, nourishment demand may include a user requirement of 65 g of protein to be consumed per day. Nourishment demand 148 may be determined as a function of receiving a nourishment goal. As used in this disclosure a "nourishment goal" is a recommended amount of nutrients that a user should consume. Nourishment goal may be identified by one or more organizations that relate to, represent, and/or study metabolic functions in humans, such as American Medical Association, American Society for Metabolic and Bariatric Surgery, Association of Metabolic Syndrome, The Association of Metabolic Syndrome and Urolithiasis, and the like thereof. Computing device 104 determines a metabolic divergence as a function of the nourishment goal and metabolic panel 116. As used in this disclosure a "metabolic divergence" is a quantitative value comprising the magnitude of divergence of metabolic panel 116 and nourishment goal. As a non-limiting example, metabolic divergence may be 23 for a nourishment goal of 23 g of fiber per day, wherein the metabolic panel identifies a low fiber concentration in the user's body. Metabolic divergence may include a transgression parameter. As used in this disclosure a "transgression parameter" is a parameter that identifies one or more divergences that exceed a variance limit. As a non-limiting example, transgression parameter may determine that a metabolic divergence should not exceed 10 for the biomarker dihydropyrimidine dehydrogenase. As a further non-limiting, transgression parameter may determine that a metabolic divergence should not exceed 2 for chromosome 2q37.

Still referring to FIG. 1, computing device 104 identifies edible 136 as a function of nourishment composition 140, nourishment demand 148, and an edible machine-learning model 152. As used in this disclosure a "edible machine-learning model" is a machine-learning model to produce an edible output given nourishment compositions and nourishment deficiencies as inputs; this is in contrast to a non-machine learning software program where the commands to be executed are determined in advance by a user and written in a programming language. Edible machine-learning model 152 may include one or more edible machine-learning processes such as supervised, unsupervised, or reinforcement machine-learning processes that computing device 104 and/or a remote device may or may not use in the determination of edible 136. As used in this disclosure a "remote device" is an external device to computing device 104. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure an "edible training set" is a training set that correlates at least nourishment composition and demand to an edible. For example, and without limitation, nourishment composition of 12 g of linear sulfated polysaccharides and a nourishment demand of low levels of carrageenan as a function of Hunter syndrome may relate to an edible of cottage cheese. The edible training set may be received as a function of user-entered valuations of nourishment compositions, nourishment demands, and/or edibles. Computing device 104 may receive edible training set by receiving correlations of nourishment compositions and/or nourishment demands that were previously received and/or determined during a previous iteration of determining edibles. The edible training set may be received by one or more remote devices that at least correlate a nourishment composition and nourishment demand to an edible, wherein a remote device is an external device to computing device 104, as described above. Edible training set may be received by one or more user-entered correlations of an nourishment composition and/or nourishment demand to an edible. Additionally or alternatively, a user may include an informed advisor, wherein an informed advisor may include, without limitation, endocrinologists, metabolic physicians, functional medicine practitioners, chemical pathologists, cardiovascular physicians, family physicians, family physicians, and the like thereof.

Still referring to FIG. 1, edible machine-learning model 140 may identify edible 120 as a function of one or more classifiers. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may receive edible machine-learning model 140 from a remote device that utilizes one or more edible machine learning processes, wherein remote device is described above in detail. For example, and without limitation, remote device may include a computing device, external device, processor, and the like thereof. Remote device may perform the edible machine-learning process using the edible training set to generate edible 136 and transmit the output to computing device 104. Remote device may transmit a signal, bit, datum, or parameter to computing device 104 that at least relates to edible 136. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified nourishment demand. Additionally or alternatively, the updated machine learning model may be transmitted to the remote device, wherein the remote device may replace the edible machine-learning model with the updated machine-learning model and determine the edible as a function of the nourishment demand using the updated machine-learning model. The updated machine-learning model may be transmitted by the remote device and received by computing device 104 as a software update, firmware update, or corrected edible machine-learning model. For example, and without limitation an edible machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device 104 may identify edible as a function of a likelihood parameter. As used in this disclosure a "likelihood parameter" is a parameter that identifies the probability of a user to consume an edible. As a non-limiting example likelihood parameter may identify a high probability that a user will consume an edible of chicken. As a further non-limiting example likelihood parameter may identify a low probability that a user will consume an edible of anchovies. Likelihood parameter may be determined as a function of a user taste profile. As used in this disclosure a "user taste profile" is a profile of a user that identifies one or more desires, preferences, wishes, and/or wants that a user has. As a non-limiting example a user taste profile may include a user's preference for chicken flavor and/or crunchy textured edibles. Likelihood parameter may be determined as a function of an edible profile. As used in this disclosure an "edible profile" is taste of an edible is the sensation of flavor perceived in the mouth and throat on contact with the edible. Edible profile may include one or more flavor variables. As used in this disclosure a "flavor variable" is a variable associated with the distinctive taste of an edible, wherein a distinctive may include, without limitation sweet, bitter, sour, salty, umami, cool, and/or hot. Edible profile may be determined as a function of receiving flavor variable from a flavor directory. As used in this disclosure a "flavor directory" is a database of flavors for an edible. As a non-limiting example flavor directory may include a list and/or collection of edibles that all contain umami flavor variables. As a further non-limiting example flavor directory may include a list and/or collection of edibles that all contain sour flavor variables. Likelihood parameter may alternatively or additionally include any user taste profile and/or edible profile used as a likelihood parameter as described in U.S. Nonprovisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 generates a nourishment program 156 as a function of edible 136 and a metabolic outcome 160 using a nourishment machine-learning model 164. As used in this disclosure a "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 156 may consist of recommending oysters for 8 days. As a further non-limiting example nourishment program 156 may recommend tofu for a first day, milk and cookies for a second day, and artichokes for a third day. Nourishment program 156 may include one or more diet programs such as paleo, keto, vegan, vegetarian, and the like thereof. Computing device 104 develops nourishment program as a function of a metabolic outcome 160. As used in this disclosure a "metabolic outcome" is an outcome that an edible may generate according to a predicted and/or purposeful plan. As a non-limiting example, metabolic outcome 160 may include a treatment outcome. As used in this disclosure a "treatment outcome" is an intended outcome that is designed to at least reverse and/or eliminate metabolic component 108 associated with metabolic panel 116 and/or metabolic dysfunction. As a non-limiting example, a treatment outcome may include reversing the effects of the metabolic dysfunction Krabbe disease. As a further non-limiting example, a treatment outcome includes reversing the metabolic dysfunction of Gaucher disease. Metabolic outcome 160 may include a prevention outcome. As used in this disclosure a "prevention outcome" is an intended outcome that is designed to at least prevent and/or avert metabolic component 108 associated with metabolic panel 116 and/or metabolic dysfunction. As a non-limiting example, a prevention outcome may include preventing the development of the metabolic dysfunction of maple syrup urine disease.

Still referring to FIG. 1, computing device 104 develops nourishment program 156 as a function of edible 136 and metabolic outcome 160 using a nourishment machine-learning model 164. As used in this disclosure a "nourishment machine-learning model" is a machine-learning model to produce a nourishment program output given edibles and/or profile outcomes as inputs; this is in contrast to a non-machine learning software program where the commands to be executed are determined in advance by a user and written in a programming language. Nourishment machine-learning model 164 may include one or more nourishment machine-learning processes such as supervised, unsupervised, or reinforcement machine-learning processes that computing device 104 and/or a remote device may or may not use in the development of nourishment program 156. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates a metabolic outcome to an edible. The nourishment training set may be received as a function of user-entered edibles, metabolic outcomes, and/or nourishment programs. For example, and without limitation, a metabolic outcome of treating mitochondrial encephalopathy may correlate to an edible of kale. Computing device 104 may receive nourishment training by receiving correlations of profile outcomes and/or edibles that were previously received and/or determined during a previous iteration of developing nourishment programs. The nourishment training set may be received by one or more remote devices that at least correlate a profile outcome and/or edible to a nourishment program, wherein a remote device is an external device to computing device 104, as described above. Nourishment training set may be received in the form of one or more user-entered correlations of a metabolic outcome and/or edible to a nourishment program. Additionally or alternatively, a user may include an informed advisor, wherein an informed advisor may include, without limitation, endocrinologists, metabolic physicians, functional medicine practitioners, chemical pathologists, cardiovascular physicians, family physicians, family physicians, and the like thereof.

Still referring to FIG. 1, computing device 104 may receive nourishment machine-learning model 152 from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to develop nourishment program 144 and transmit the output to computing device 104. The remote device may transmit a signal, bit, datum, or parameter to computing device 104 that at least relates to nourishment program 144. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new profile outcome that relates to a modified edible. Additionally or alternatively, the updated machine learning model may be transmitted to the remote device, wherein the remote device may replace the nourishment machine-learning model with the updated machine-learning model and develop the nourishment program as a function of the profile outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a neural net machine-learning process, wherein the updated machine-learning model may incorporate decision tree machine-learning processes.

Figure 2:
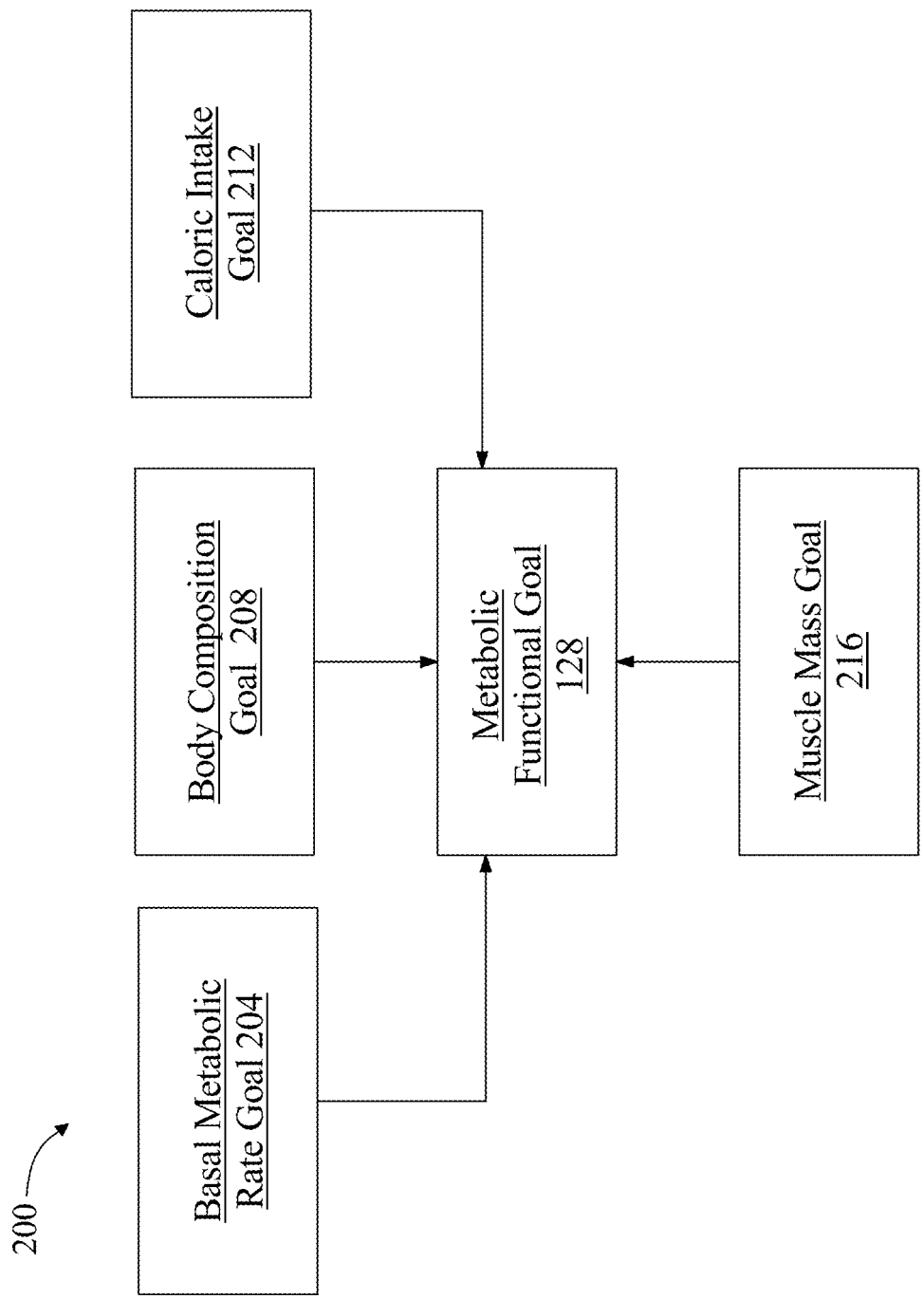
FIG. 2 is a block diagram of an exemplary embodiment of a metabolic functional goal according to an embodiment of the invention.

Now referring to FIG. 2, an exemplary embodiment 200 of a metabolic functional goal 128 according to an embodiment of the invention is illustrated. Metabolic functional goal 128 may include a basal metabolic rate goal 204. As used in this disclosure a "basal metabolic rate goal" is a desired amount of calories and/or energy that a user would like to expend throughout the day. As a non-limiting example, basal metabolic rate goal may include a user that expends 2,060 Calories per day, wherein the user desires to expend 2,200 Calories per day. Metabolic functional goal 128 may include a body composition goal 208. As used in this disclosure a "body composition goal" is a desired proportion of fat and non-fat mass in the user's body. As a non-limiting example body composition goal 208 may include a user desire to have a body composition of 8% body fat, 53% water, 32% muscle mass, and 8% bone mass. Metabolic functional goal 128 may include a caloric intake goal 212. As used in this disclosure a "caloric intake goal" is a desired amount of calories that a user would like to consume throughout the day. As a non-limiting example, caloric intake goal 212 may include a user that desires to consume 1,600 calories per day. Metabolic functional goal 128 may include a muscle mass goal 216. As used in this disclosure a "muscle mass goal" is a user desired muscle mass for skeletal muscle, smooth muscle, and/or cardiac muscle. As a non-limiting example, muscle mass goal 216 may include a user desire to gain 22 lbs. and/or 9.98 kg of skeletal muscle.

Figure 3:
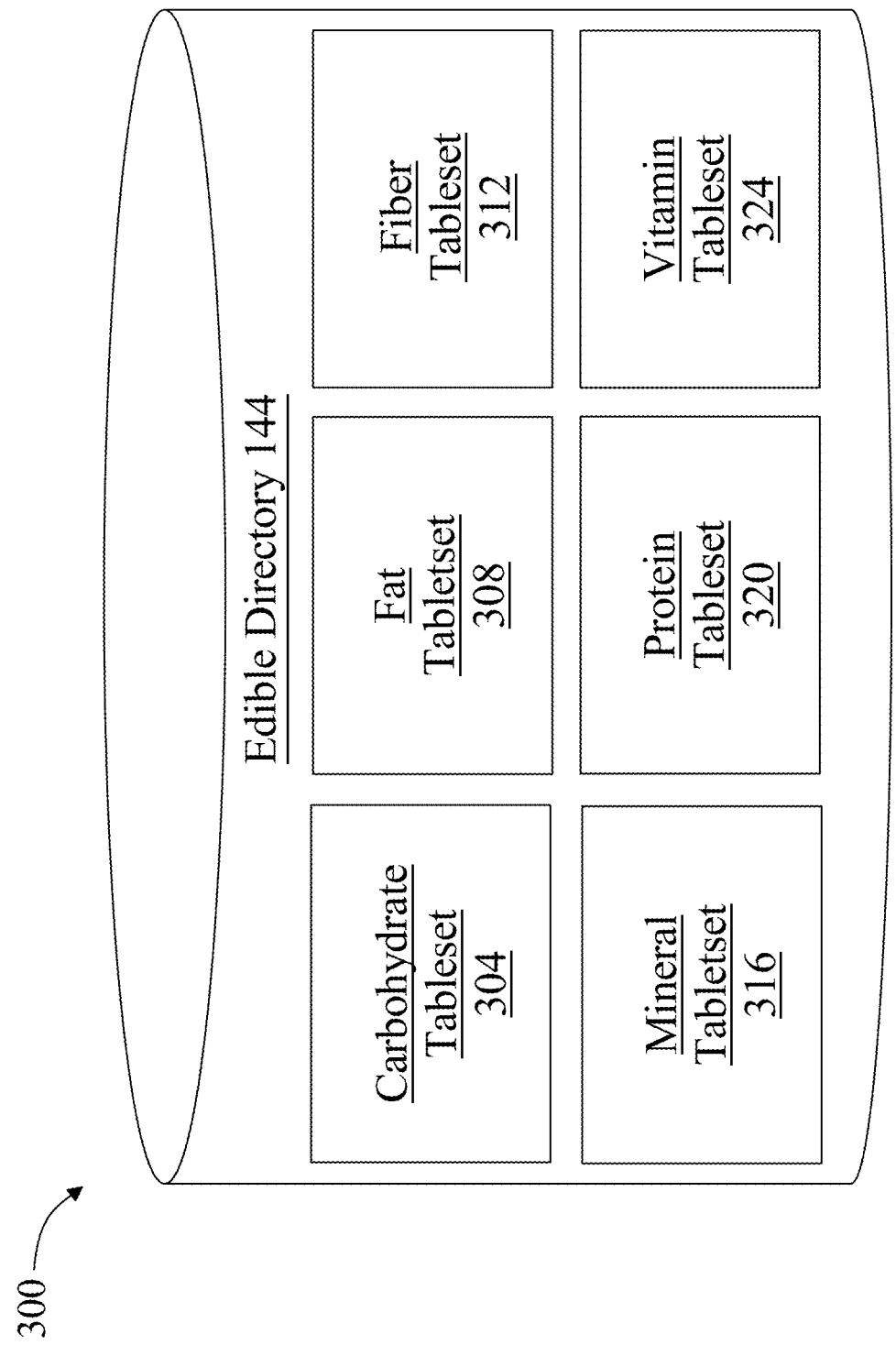
FIG. 3 is a block diagram of an exemplary embodiment of an edible directory according to an embodiment of the invention.

Now referring to FIG. 3, an exemplary embodiment 300 of an edible directory 144 according to an embodiment of the invention is illustrated. Edible directory 144 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 144 may alternatively or additionally be implemented using a distributed data storage protocol and/or data structure, such as a distributed hash table or the like. Edible directory 144 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 144 may include a carbohydrate tableset 304. Carbohydrate tableset 304 may relate to a nourishment composition of an edible with respect to the quantity and/or type of carbohydrates in the edible. As a non-limiting example, carbohydrate tableset 304 may include monosaccharides, disaccharides, oligosaccharides, polysaccharides, and the like thereof. Edible directory 144 may include a fat tableset 308. Fat tableset 308 may relate to a nourishment composition of an edible with respect to the quantity and/or type of esterified fatty acids in the edible. Fat tableset 308 may include, without limitation, triglycerides, monoglycerides, diglycerides, phospholipids, sterols, waxes, and free fatty acids. Edible directory 144 may include a fiber tableset 312. Fiber tableset 312 may relate to a nourishment composition of an edible with respect to the quantity and/or type of fiber in the edible. As a non-limiting example, fiber tableset 312 may include soluble fiber, such as beta-glucans, raw guar gum, psyllium, inulin, and the like thereof as well as insoluble fiber, such as wheat bran, cellulose, lignin, and the like thereof. Edible directory 144 may include a mineral tableset 316. Mineral tableset 316 may relate to a nourishment composition of an edible with respect to the quantity and/or type of minerals in the edible. As a non-limiting example, mineral tableset 316 may include calcium, phosphorous, magnesium, sodium, potassium, chloride, sulfur, iron, manganese, copper, iodine, zing, cobalt, fluoride, selenium, and the like thereof. Edible directory 144 may include a protein tableset 320. Protein tableset 320 may relate to a nourishment composition of an edible with respect to the quantity and/or type of proteins in the edible. As a non-limiting example, protein tableset 320 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 144 may include a vitamin tableset 324. Vitamin tableset 324 may relate to a nourishment composition of an edible with respect to the quantity and/or type of vitamins in the edible. As a non-limiting example, vitamin tableset 324 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
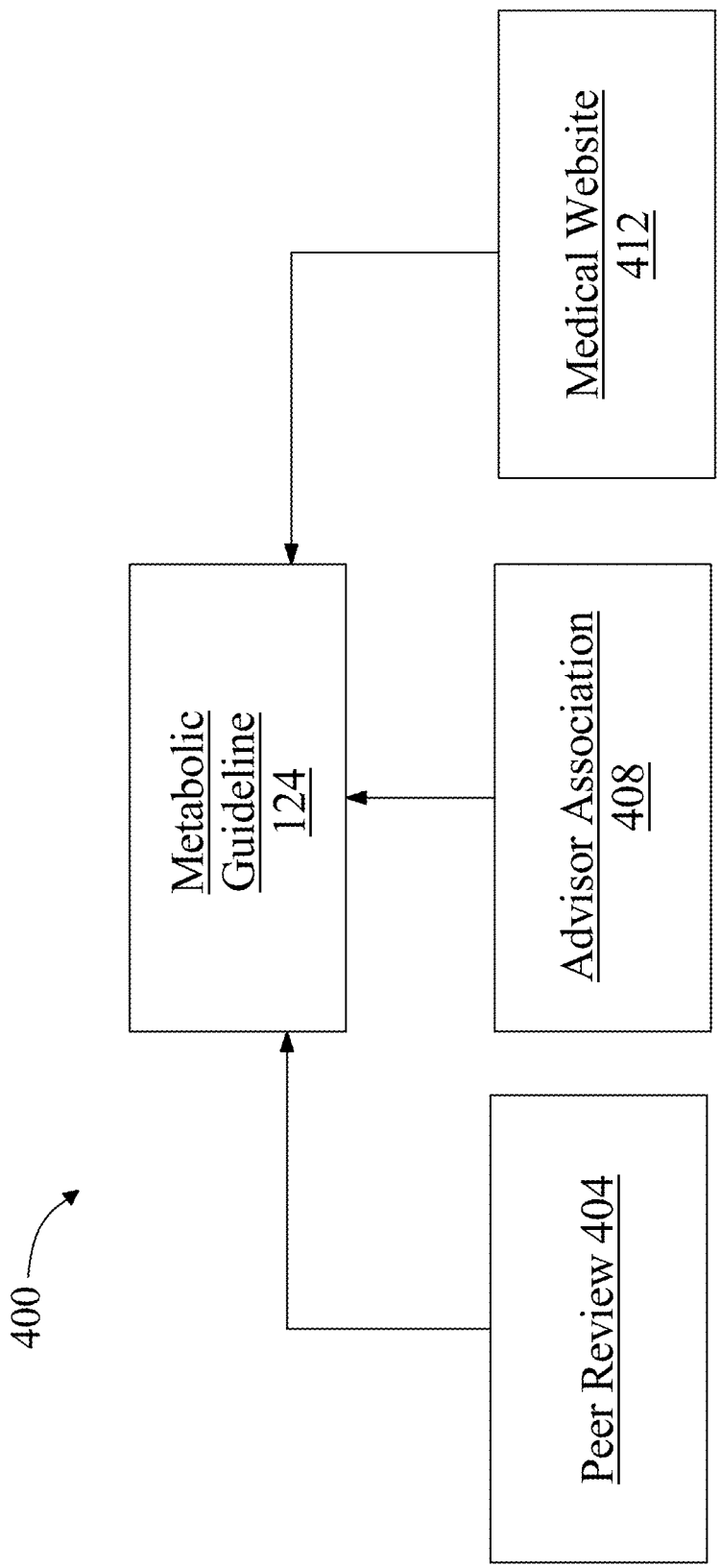
FIG. 4 is a block diagram of an exemplary embodiment of a medical guideline according to an embodiment of the invention.

Now referring to FIG. 4, an exemplary embodiment 300 of a metabolic guideline 124 according to an embodiment of the invention is illustrated. Metabolic guideline 124 may include a peer review 404. As used in this disclosure a "peer review" is a source that establishes a guideline as a function of an evaluation conducted by one or more people with similar competencies. As a non-limiting example peer review 404 may include professional peer reviews, scholarly peer reviews, government peer reviews, medical peer reviews, technical peer reviews, and the like thereof. Metabolic guideline 124 may include an informed advisor association 408. As used in this disclosure an "informed advisor association" is a source that establishes as a function of one or more committees, organizations, and/or groups that at least determine and/or organize status gradings. As a non-limiting example informed advisor association 408 may include the American Medical Association, American Society for Metabolic and Bariatric Surgery, Association of Metabolic Syndrome, The Association of Metabolic Syndrome and Urolithiasis, and the like thereof. Metabolic guideline 124 may include a medical website tableset 412. As used in this disclosure a "medical website" is a source that establishes a guideline as a function of one or more online and/or web-based medical recommendations. As a non-limiting example medical website 412 may include Medline Plus, Drugs.com, Mayo Clinic, Orphanet, Medgadget, WebMD, Health.gov, SPM ePatients blog, and the like thereof.

Figure 5:
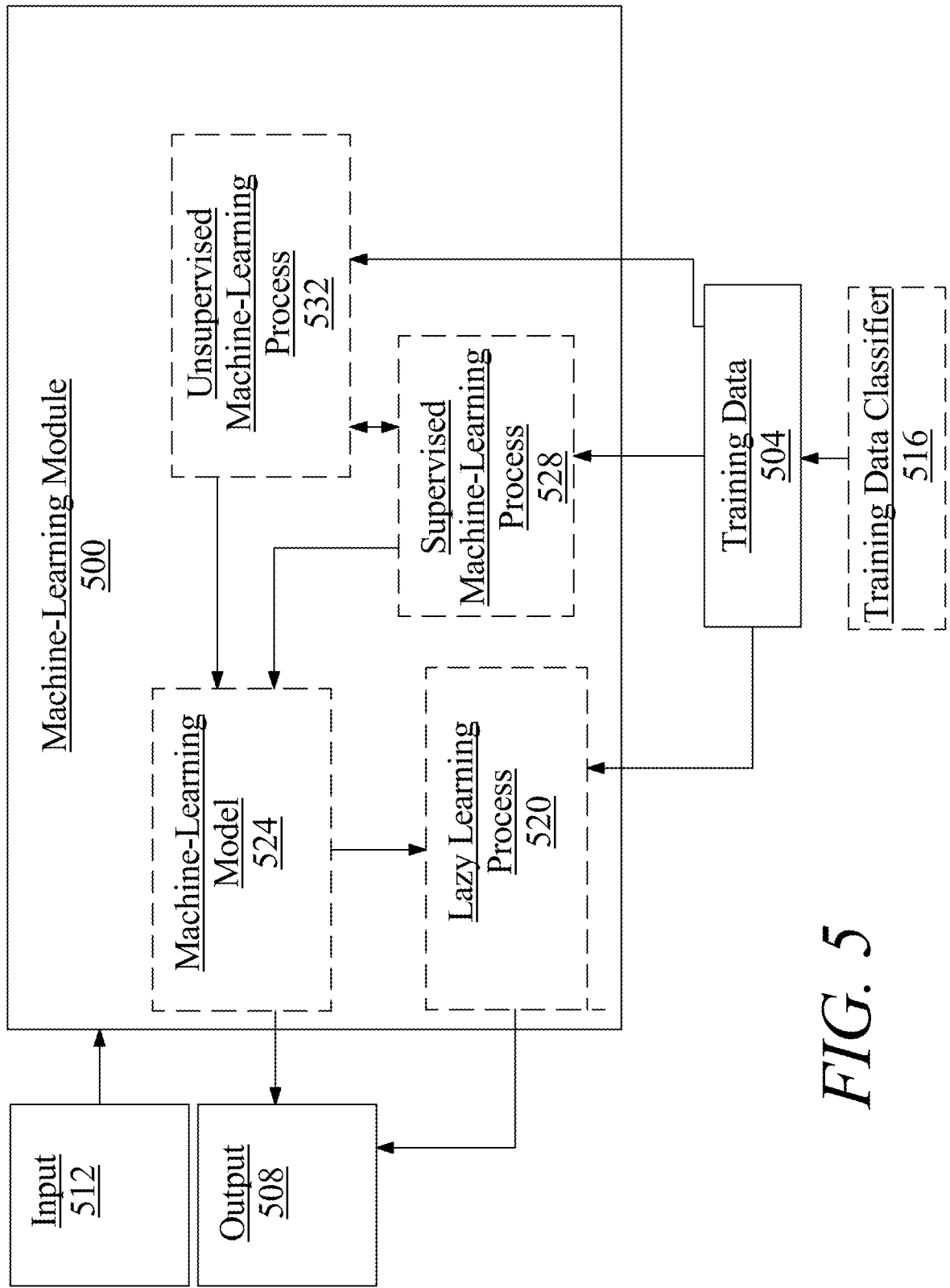
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs of status gradings, metabolic functional goals, and metabolic components may output metabolic panels.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories including a health status grading relating to a low, medium and/or high health status.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include status gradings, metabolic components, metabolic functional goals as described above as inputs, metabolic panels as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
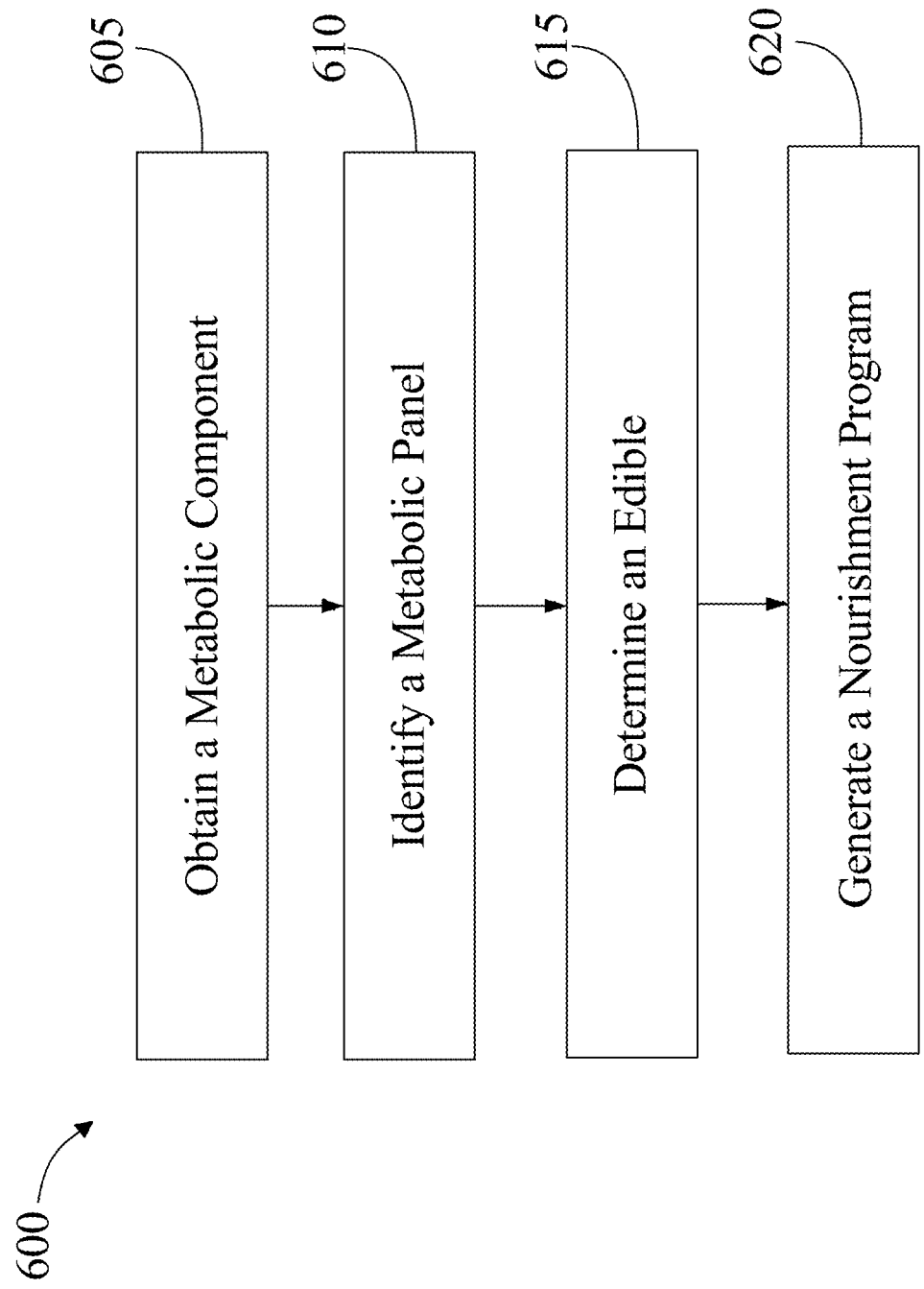
FIG. 6 is a process flow diagram illustrating an exemplary embodiment of a method of generating a metabolic dysfunction nourishment program.

Now referring to FIG. 6, an exemplary embodiment of a method 600 for generating a metabolic dysfunction nourishment program is illustrated. At step 605, a computing device 104 obtains a metabolic component 108 as a function of a user metabolic system 112. Computing device 104 includes any of the computing device 104 as described above, in reference to FIGS. 1-5. Metabolic component 108 includes any of the metabolic component 108 as described above, in reference to FIGS. 1-5. User metabolic system 112 includes any of the user metabolic system 112 as described above, in reference to FIG. 105.

Still referring to FIG. 6, at step 610, computing device 104 identifies a metabolic panel 116 as a function of metabolic component 108. Metabolic panel 116 includes any of the metabolic panel 116 as described above, in reference to FIGS. 1-5. Computing device 104 identifies metabolic panel 116 by receiving a status grading 120 as a function of a metabolic guideline 124. Status grading 120 includes any of the status grading 120 as described above, in reference to FIGS. 1-5. Metabolic guideline 124 includes any of the metabolic guideline as described above, in reference to FIGS. 1-5. Computing device 104 ascertains a metabolic functional goal 128. Metabolic functional goal 128 includes any of the metabolic functional goal 128 as described above, in reference to FIGS. 1-5. Computing device 104 identifies metabolic panel 116 as a function of status grading 120, metabolic functional goal 128, and metabolic component 108 using a metabolic machine-learning model 132. Metabolic machine-learning model 132 includes any of the metabolic machine-learning model 132 as described above in reference to FIGS. 1-5.

Still referring to FIG. 6, at step 615, computing device 104 determines an edible 136 as a function of metabolic panel 116. Edible 136 includes any of the edible 136 as described above, in reference to FIGS. 1-5. Computing device determines edible 136 by receiving a nourishment composition 140 from an edible directory 144. Nourishment composition 140 includes any of the nourishment composition 140 as described above, in reference to FIGS. 1-5. Edible directory 144 includes any of the edible directory 144 as described above, in reference to FIGS. 1-5. Computing device 104 produces a nourishment demand 148 as a function of metabolic panel 116. Nourishment demand 148 includes any of the nourishment demand 148 as described above, in reference to FIGS. 1-5. Computing device 104 determines edible 136 as a function of nourishment composition 140 and nourishment demand 148 using an edible machine-learning model 152. Edible machine-learning model 152 includes any of the edible machine-learning model 152 as described above in reference to FIGS. 1-5.

Still referring to FIG. 6, at step 620, computing device 104 generates a nourishment program 156 as a function of edible 136 and a metabolic outcome 160 using a nourishment machine-learning model 164. Nourishment program 156 includes any of the nourishment program 156 as described above, in reference to FIGS. 1-5. Metabolic outcome 160 includes any of the metabolic outcome 160 as described above, in reference to FIGS. 1-5. Nourishment machine-learning model 164 includes any of the nourishment machine-learning model 164 as described above in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
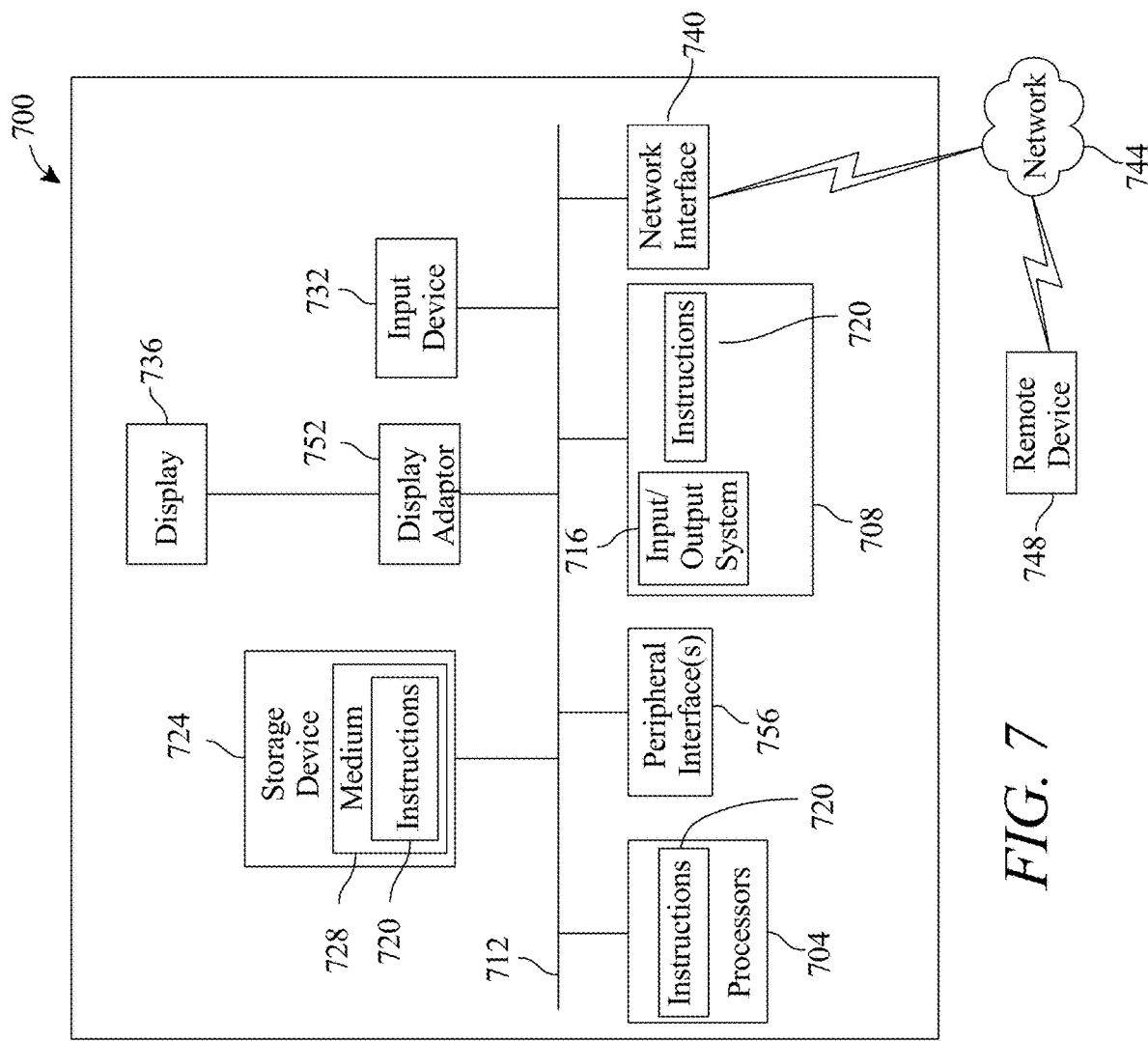
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a metabolic dysfunction nourishment program, the system comprising:
 a computing device, the computing device configured to:
  obtain a metabolic component from an input as a function of an informed advisor and a medical assessment as evidencing a condition of a metabolic system of a user;
  identify a metabolic panel as a function of the metabolic component, wherein identifying further comprises:
   receiving a status grading as a function of a metabolic guideline;
   ascertaining a metabolic dysfunction present in the user;
   ascertaining a basal metabolic rate goal;
   ascertaining a body composition goal; and
   specifying which parameters of metabolic panel data to obtain as a function of a metabolic machine-learning model, wherein the specifying comprises:
    receiving metabolic training data, wherein the training data correlates metabolic component to metabolic panel;
    training the metabolic machine-learning model using the metabolic training data;
    specifying which parameters of metabolic panel data to obtain as a function of the metabolic panel data and the metabolic machine-learning; and
    providing an updated metabolic machine-learning model, which incorporates a new metabolic component that relates to a modified basal metabolic rate goal;
  determine an edible to be consumed by the user as a function of metabolic panel data obtained, wherein determining the edible further comprises:
   receiving a nourishment composition from an edible directory, wherein the edible directory comprises a database of edibles identified as a function of one or more metabolic components and arranged in a distributed hash table, wherein the distributed hash table includes a plurality of nourishment composition tablesets;
   producing a nourishment demand as a function of the metabolic panel, wherein producing the nourishment demand further comprises:
    receiving a nourishment goal;
    ascertaining a metabolic divergence as a function of the nourishment goal and a metabolic panel, wherein the metabolic divergence includes a transgression parameter, wherein the transgression parameter identifies a variance limit of the metabolic divergence for a chromosome; and
    producing the nourishment demand as a function of the metabolic divergence; and
   determining the edible as a function of the nourishment composition, the ascertained metabolic dysfunction, and the nourishment demand using an edible machine-learning model; and
  generate a nourishment program as a function of the edible and a desired metabolic outcome using a nourishment machine-learning model.

2. The system of claim 1, wherein the metabolic component includes a biomarker.

3. The system of claim 1, wherein obtaining the metabolic component includes receiving an input from a user and obtaining the metabolic component as a function of the input.

4. The system of claim 1, wherein ascertaining the metabolic dysfunction further comprises:
 obtaining a dysfunction training set that relates a metabolic enumeration and a metabolic system effect; and
 identifying the metabolic dysfunction as a function of the metabolic component using a dysfunction machine-learning model, wherein the dysfunction machine-learning model is trained as a function of the dysfunction training set.

5. The system of claim 1, wherein determining the edible further comprises:
generating a likelihood parameter, wherein the likelihood parameter relates a user taste profile to an edible profile; and
specifying the edible as a function of the likelihood parameter.

6. The system of claim 5, wherein specifying the edible further comprises receiving a flavor variable from a flavor directory and specifying the edible profile as a function of the flavor variable.

7. The system of claim 1, wherein the metabolic outcome includes a treatment outcome.

8. The system of claim 1, wherein the metabolic outcome includes a prevention outcome.

9. The system of claim 1, wherein the chromosome is chromosome 2q37.

10. A method for generating a metabolic dysfunction nourishment program, the method comprising:
obtaining, by a computing device, a metabolic component from an input as a function of an informed advisor and a medical assessment a condition of metabolic system of a user;
configuring by the computing device, a metabolic panel as a function of the metabolic component, wherein configuring further comprises:
receiving a status grading as a function of a metabolic guideline;
ascertaining a basal metabolic rate goal;
ascertaining a metabolic dysfunction present in the user;
ascertaining a body composition goal; and
specifying parameters of metabolic panel data to obtain as a function of a metabolic machine-learning model, wherein the specifying comprises:
receiving metabolic training data, wherein the training data correlates metabolic component to metabolic panel;
training the metabolic machine-learning model using the metabolic training data;
specifying which parameters of metabolic panel data to obtain as a function of the metabolic panel data and the metabolic machine-learning; and
providing an updated metabolic machine-learning model, which incorporates a new metabolic component that relates to a modified basal metabolic rate goal;
specifying, by the computing device, an edible to be consumed by the user as a function of the metabolic panel data obtained, wherein specifying the edible further comprises:
receiving a nourishment composition from an edible directory, wherein the edible directory comprises a database of edibles identified as a function of one or more metabolic components and arranged in a distributed hash table, wherein the distributed hash table includes a plurality of nourishment composition tablesets;
producing a nourishment demand as a function of the metabolic panel, wherein producing the nourishment demand further comprises:
receiving a nourishment goal;
ascertaining a metabolic divergence as a function of the nourishment goal and a metabolic panel, wherein the metabolic divergence includes a transgression parameter, wherein the transgression parameter identifies a variance limit of the metabolic divergence for a chromosome; and
producing the nourishment demand as a function of the metabolic divergence; and
specifying the edible as a function of the nourishment composition, the ascertained metabolic dysfunction, and the nourishment demand using an edible machine-learning model; and
generating, by the computing device, a nourishment program as a function of the edible and a desired metabolic outcome using a nourishment machine-learning model.

11. The method of claim 10, wherein the metabolic component includes a biomarker.

12. The method of claim 10, wherein obtaining the metabolic component includes receiving an input from a user and obtaining the metabolic component as a function of the input.

13. The method of claim 10, wherein identifying the metabolic dysfunction further comprises:
obtaining a dysfunction training set that relates a metabolic enumeration and a metabolic system effect; and
determining the metabolic dysfunction as a function of the metabolic component using a dysfunction machine-learning model, wherein the dysfunction machine-learning model is trained as a function of the dysfunction training set.

14. The method of claim 10, wherein specifying the edible further comprises:
generating a likelihood parameter, wherein the likelihood parameter relates a user taste profile to an edible profile; and
specifying the edible as a function of the likelihood parameter.

15. The method of claim 14, wherein specifying the edible further comprises receiving a flavor variable from a flavor directory and specifying the edible profile as a function of the flavor variable.

16. The method of claim 10, wherein the metabolic outcome includes a treatment outcome.

17. The method of claim 10, wherein the metabolic outcome includes a prevention outcome.

18. The method of claim 10, wherein the chromosome is chromosome 2q37.

* * * * *